United States Patent

Better et al.

[11] Patent Number: 5,264,650
[45] Date of Patent: Nov. 23, 1993

[54] SULFOLANE PURIFICATION BY HYDROCARBON EXTRACTION

[75] Inventors: Michael A. Better, Deptford; Jonathan E. Child, Sewell; Kenneth J. Del Rossi, Woodbury; Edward H. Edelson, Cherry Hill; Anagha A. Gupte, Marlton; Rafi Jalkian, Mantua; Tomas R. Melli, Sewell, all of N.J.; Sergei Yurchak, Media, Pa.

[73] Assignee: Mobil Oil Corporation, Fairfax, Va.

[21] Appl. No.: 991,919

[22] Filed: Dec. 17, 1992

Related U.S. Application Data

[63] Continuation-in-part of Ser. No. 833,684, Feb. 11, 1992, Pat. No. 5,191,150.

[51] Int. Cl.$^5$ ............................ C07C 2/68; C07C 7/10
[52] U.S. Cl. .................................. 585/802; 585/723; 585/724; 585/857
[58] Field of Search ............... 585/723, 724, 802, 857

[56] References Cited

U.S. PATENT DOCUMENTS

| | | | |
|---|---|---|---|
| 3,795,712 | 3/1974 | Torck | 585/724 |
| 4,014,953 | 3/1977 | Brown, Jr. | 585/724 |
| 4,058,575 | 11/1977 | Cahn et al. | 585/724 |
| 4,199,409 | 4/1980 | Skraba | 585/724 |
| 4,317,795 | 3/1982 | Makovec et al. | 422/111 |
| 4,663,026 | 5/1987 | Louie et al. | 585/723 |
| 5,191,150 | 3/1993 | Child et al. | 585/809 |

Primary Examiner—Asok Pal
Attorney, Agent, or Firm—Alexander J. McKillop; Dennis P. Santini; Robert B. Furr, Jr.

[57] ABSTRACT

The present invention provides a method for separating conjunct polymers which are formed as byproducts of acid catalyzed isoparaffin-olefin alkylation and sulfolane from a mixture containing conjunct polymers, sulfolane, and hydrofluoric acid comprising the sequential steps of:

(a) separating hydrofluoric acid from a mixture containing conjunct polymers, sulfolane, and hydrofluoric acid to provide a first intermediate stream containing less than about 30 percent hydrofluoric acid by weight;

(b) mixing said intermediate stream with a nonpolar extraction solvent to provide a second intermediate stream; and (c) gravitationally separating said intermediate stream into a less dense extract stream enriched in conjunct polymers and a more dense liquid stream enriched in sulfolane.

15 Claims, 3 Drawing Sheets

SULFOLANE PURIFICATION BY HYDROCARBON EXTRACTION

SULFOLANE PURIFICATION BY HYDROCARBON EXTRACTION

SULFOLANE PURIFICATION BY HYDROCARBON EXTRACTION

CROSS REFERENCE TO RELATED APPLICATIONS

This is a continuation-in-part of allowed application Ser. No. 07/833,684, filed Feb. 11, 1992. now U.S. Pat. No. 5,191,150.

This application is related by disclosure of similar subject matter to Ser. No. 07/991,918, filed Dec. 17, 1992, Ser. No. 07/991,920, filed Dec. 17, 1992, Ser. No. 07/991,921, filed Dec. 17, 1992, and Ser. No. 07/991,922, filed Dec. 17, 1992, filed on even date herewith, all allowed on even date.

FIELD OF THE INVENTION

The present invention relates to the art of catalytic alkylation. More specifically, the invention relates to a liquid alkylation catalyst and an isoparaffin-olefin alkylation process. Particularly, the invention provides a liquid alkylation catalyst composition which avoids many of the safety and environmental concerns associated with concentrated hydrofluoric acid.

BACKGROUND OF THE INVENTION

Alkylation is a reaction in which an alkyl group is added to an organic molecule. Thus an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate. This alkylate is a valuable blending component in the manufacture of gasolines due not only to its high octane rating but also to its sensitivity to octane-enhancing additives.

Industrial alkylation processes have historically used concentrated hydrofluoric or sulfuric acid catalysts under relatively low temperature conditions. Acid strength is preferably maintained at 88 to 94 weight percent by the continuous addition of fresh acid and the continuous withdrawal of spent acid. As used herein, the term "concentrated hydrofluoric acid" refers to an essentially anhydrous liquid containing at least about 85 weight percent HF.

Hydrofluoric and sulfuric acid alkylation processes share inherent drawbacks including environmental and safety concerns, acid consumption, and sludge disposal. For a general discussion of sulfuric acid alkylation, see the series of three articles by L. F. Albright et al., "Alkylation of Isobutane with $C_4$ Olefins", 27 *Ind. Eng. Chem. Res.*, 381-397, (1988). For a survey of hydrofluoric acid catalyzed alkylation, see 1 *Handbook of Petroleum Refining Processes* 23-28 (R. A. Meyers, ed., 1986).

Hydrogen fluoride, or hydrofluoric acid (HF) is highly toxic and corrosive. However, it is used as a catalyst in isomerization, condensation, polymerization and hydrolysis reactions. The petroleum industry used anhydrous hydrogen fluoride primarily as a liquid catalyst for alkylation of olefinic hydrocarbons to produce alkylate for increasing the octane number of gasoline. Years of experience in its manufacture and use have shown that HF can be handled safely, provided the hazards are recognized and precautions taken. Though many safety precautions are taken to prevent leaks, massive or catastrophic leaks are feared primarily because the anhydrous acid will fume on escape creating a vapor cloud that can be spread for some distance.

Previous workers in this field approached this problem from the standpoint of containing or neutralizing the HF cloud after its release.

U.S. Pat. Nos. 4,938,935 and 4,985,220 to Audeh and Greco, as well as U.S. Pat. No. 4,938,936 to Yan teach various methods for containing and/or neutralizing HF acid clouds following accidental releases.

But it would be particularly desirable to provide an additive which decreases the cloud forming tendency of HF without compromising its activity as an isoparaffin-olefin alkylation catalyst. Solvents and complexing agents for hydrofluoric acid have, in the past, been disclosed for various purposes as noted in the following references.

U.S. Pat. No. 2,615,908 to McCaulay teaches thioether-HF-copper complex compounds and a method for preparing the same. Potential uses for the thioether-HF-copper composition compounds are listed from column 6, line 55 through column 8 at line 3. The method is said to be useful for purifying HF-containing vent gases from an industrial HF alkylation plant. See column 7, lines 10-24.

U.S. Pat. No. 3,531,546 to Hervert discloses a HF-$CO_2$ catalyst composition which is said to be useful for alkylation as well as olefin isomerization.

U.S. Pat. No. 3,795,712 to Torck et al. relates to acid catalysts comprising a Lewis acid, a Bronsted acid, and a sulfone of the formula $R—SO_2—R'$, where R and R' are each separately a monovalent radical containing from 1 to 8 carbon atoms or form together a divalent radical having from 3 to 12 carbon atoms.

U.S. Pat. No. 3,856,764 to Throckmorton et al. teaches an olefin polymerization catalyst comprising (1) at least one organoaluminum compound, (2) at least one nickel compound selected from the class consisting of nickel salts of carboxylic acids, organic complex compounds of nickel, or nickel tetracarbonyl and (3) at least one hydrogen fluoride complex prepared by complexing hydrogen fluoride with a member of the class consisting of ketones, ethers, esters, alcohols, nitriles, and water.

U.S. Pat. Nos. 4,025,577 and 4,099,924 to Siskin et al. report the use of alkylation catalyst compositions containing HF, a metal halide, and sulfolane. U.S. Patent to Olah relates to an additive formulation which reduces the fuming tendency of HF.

Promoters such as alcohols, thiols, water, ethers, thioethers, sulfonic acids, and carboxylic acids are disclosed in combination with strong Bronsted acids such as HF, fluorosulfonic and trihalomethanesulfonic acids in U.S. Pat. No. 3,778,489 to Parker et al. The promoters are said to modify the activity of the strong Bronsted acids for alkylation.

The preceding references demonstrate the desirability of a liquid Bronsted acid catalyst (such as HF) for isoparaffin-olefin alkylation, as well the utility of liquid Bronsted acids in combination with metal halides, particularly metal fluorides.

In U.S. application Ser. No. 07/719,879, filed Jun. 21, 1991, now abandoned. An isoparaffin-olefin alkylation process is disclosed which uses an HF/sulfolane catalyst containing relatively high concentrations of sulfolane, and is incorporated by reference for the details of isoparaffin-olefin alkylation with a sulfolane-enriched HF catalyst. Allowed U.S. application Ser. No. 07/833,684, filed Feb. 11, 1992 now U.S. Pat. No. 5,191,150, relates to a method for separating mixtures containing HF, sulfolane, and the conjunct polymeric byproducts of HF-catalyzed isoparaffin-olefin alkylation which are commonly referred to as acid soluble oil, or ASO.

Isoparaffin-olefin alkylation processes typically convert at least a portion of the feedstock to conjunct polymeric byproducts, which are more commonly referred to as acid soluble oil or ASO. Adding sulfolane to HF for isoparaffin-olefin alkylation complicates the problem of removing ASO from the system because the typical boiling range of the ASO brackets the boiling point of sulfolane (285° C.). Thus sulfolane cannot be readily separated from ASO by distillation.

SUMMARY OF THE INVENTION

The present invention provides a method for separating sulfolane from the conjunct polymeric byproducts formed in HF/sulfolane-catalyzed isoparaffin-olefin alkylation. The method of the invention extracts ASO from a stripped mixture containing ASO, sulfolane, alkylate, and HF to form (a) a less dense stream containing the extraction solvent enriched in ASO; and (b) a more dense stream enriched in sulfolane.

The present invention comprises the sequential steps of:

(a) removing hydrofluoric acid from a mixture containing sulfolane, ASO and hydrofluoric acid to provide a first intermediate stream containing less than about 30 percent hydrofluoric acid by weight;

(b) mixing said intermediate stream with a nonpolar extraction solvent to provide a second intermediate stream; and (c) gravitationally separating said intermediate stream into a less dense extract stream enriched in ASO and a more dense liquid stream enriched in sulfolane.

The method finds particular utility in regenerating an HF/sulfolane catalyst used in an isoparaffin-olefin alkylation process. The hydrofluoric acid concentration of the mixture is preferably decreased by stripping. While any suitable inert stripping fluid may be employed, an isoparaffin is preferred, and an isoparaffin suitable for isoparaffin-olefin alkylation such as isobutane is still more preferred. Two sequential stripping steps may be used, as the sulfolane/extract solvent phases appear to separate more readily as the hydrofluoric acid concentration is decreased. If two-stage stripping is used, a second inert stripping fluid such as nitrogen is preferred.

The method of the invention requires removing hydrofluoric acid to provide an intermediate stream containing no more than 30 weight percent hydrofluoric acid before adding the nonpolar extraction solvent. Extraction performance improves as the hydrofluoric acid content is decreased, with intermediate stream hydrofluoric acid concentrations preferably falling below 25 percent by weight, more preferably below about 10 percent hydrofluoric acid by weight, and most preferably below about 5 percent by weight. The hydrofluoric acid must be removed before the liquid extraction step; the sequence of these two steps is critical in the present method.

The conjunct polymeric byproducts of liquid acid catalyzed isoparaffin-olefin alkylation are understood to comprise a complex mixture, but the mechanism underlying the present invention is not well understood. To effectively extract ASO from a mixture of HF, sulfolane, and ASO, the mixture must contain less than 30 weight percent HF. The composition of the extraction solvent, on the other hand, is less critical. The extraction solvent may comprise any substantially nonpolar organic which is immiscible with a mixture of sulfolane, HF, and ASO containing less than about 30 weight percent HF. Nonpolar extraction solvents useful in the present invention are characterized by a dipole moment ($\mu$) of less than about 0.6 debyes. Examples of useful nonpolar extraction solvents include aliphatic hydrocarbons containing from about 4 to about 12 carbon atoms (e.g., isobutane ($\mu=0$), isopentane ($\mu=0$), n-pentane ($\mu=0$), and isooctane ($\mu=0$)), and as well as aromatic hydrocarbons containing from about 6 to about 20 carbon atoms (e.g., m-xylene ($\mu=0.37$), toluene ($\mu=0.36$), and ethylbenzene ($\mu=0.59$). Preferred nonpolar extraction solvents include the isoparaffins, e.g. $C_4$-$C_8$ isoparaffins, and paraffinic mixtures containing one or more of these isoparaffins. Isobutane and the trimethylpentane-rich alkylate alkylate product formed by reacting isobutane with butene are particularly preferred extraction solvents.

Temperature and pressure are maintained in the extraction and gravitational separation steps to ensure that the feed and effluent streams remain in the liquid state. Temperatures below about 200° F. are preferred, while temperatures below about 100° F. are more preferred. While temperature is not critical, the phases separate more completely at lower temperatures. Pressure is similarly not critical to the extraction and gravitational separation steps, but is preferably controlled to maintain both phases in the liquid state. Typical pressures fall within the range of from about atmospheric pressure to about 200 psig.

The extraction solvent may be charged directly to the gravitational separation zone or may be mixed with the stripped intermediate stream upstream from the gravitational separation zone. If the extraction solvent is charged directly to the gravitational separation zone, the extraction solvent preferably enters the gravitational separation zone below the liquid/liquid interface formed at the boundary between the more dense phase and the less dense phase.

EMBODIMENTS

Figure 1:
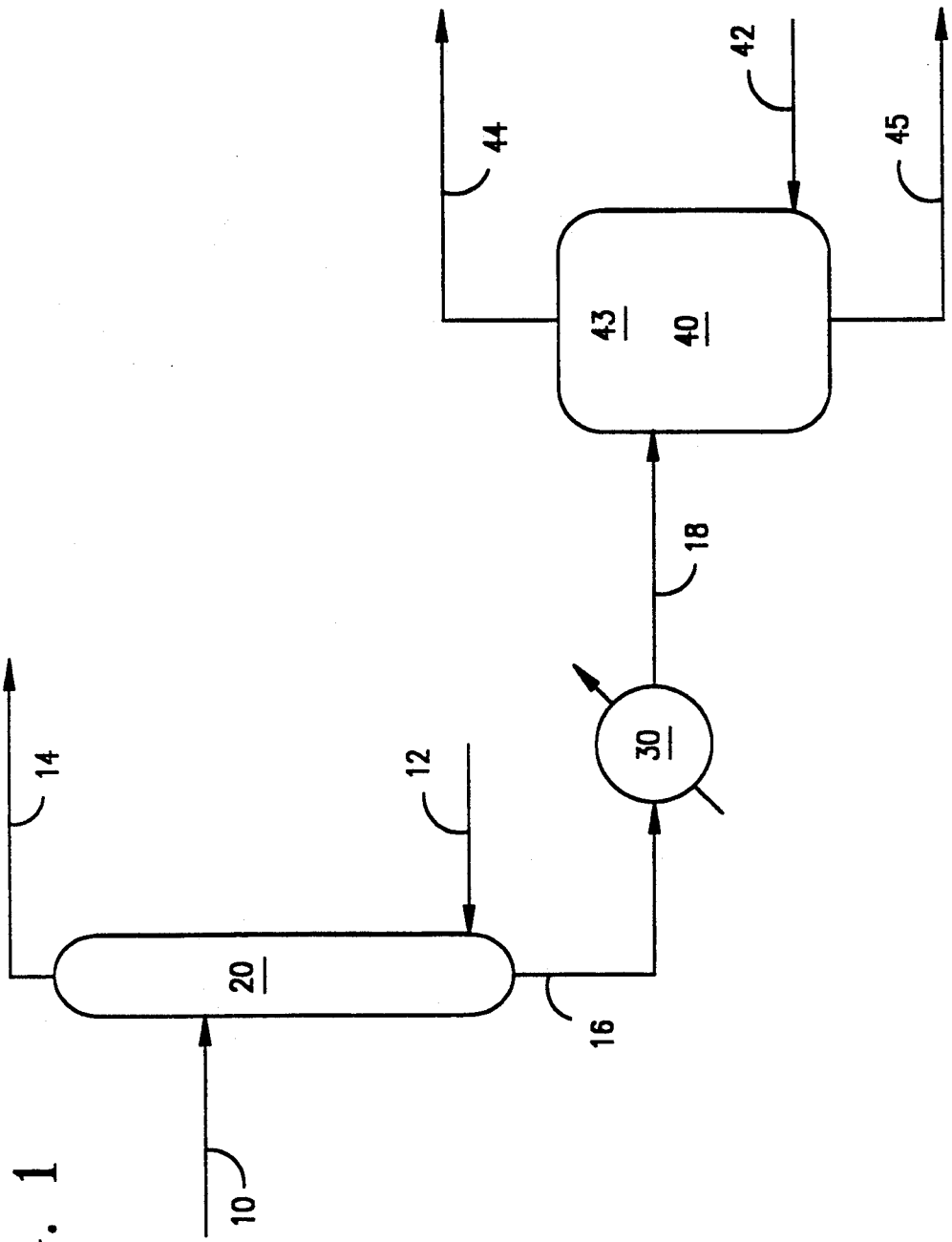
FIG. 1 is a simplified schematic diagram showing initial processing steps in the method of the invention.

Referring now to the Figure, a slipstream of spent alkylation catalyst 10 flows from an operating HF/sulfolane catalyzed isoparaffin-olefin alkylation process unit (not shown) and enters distillation/stripping tower 20. Stripping gas, for example, isobutane, enters distillation/stripping tower 20 through line 12, carries stripped HF upwardly through the tower, and exits the distillation/stripping tower 20 via overhead line 14. The HF-enriched isobutane may optionally be fractionated again, but is preferably charged directly back to the isoparaffin-olefin alkylation process unit (not shown). The distillation/stripping tower bottoms product is charged through line 16 at tower temperature of about 300° F. and flows to cooler 30. The bottoms product, cooled to about 70° F., flows through line 18 and enters gravitational separator 40 at about 100 psig.

The nonpolar extraction solvent enters gravitational separation zone 40 near the bottom of the separation zone through line 42. Two liquid phases form within gravitational separator 40. The upper, less dense phase, enriched in ASO, collects near the top 43 of gravitational separator 40, and is withdrawn through line 44 for further processing to recover the solvent. The less dense phase may heated or flashed at lower pressures to recover the solvent.

The lower, more dense liquid phase, enriched in sulfolane, flows out of gravitational separator 40 through line 45 and may be recycled directly to the alkylation process unit (not shown) without further treatment.

COMPARATIVE EXAMPLE

A mixture of hydrofluoric acid, sulfolane, and conjunct polymeric byproducts (which conjunct polymeric byproducts are evolved from the catalytic alkylation of isobutane with butene, referred to hereinafter as acid soluble oil or ASO) containing about 65 weight percent hydrofluoric acid, 30 weight percent sulfolane and about 5 weight percent ASO, is charged to a decantation vessel at ambient temperature and pressure sufficient to maintain the mixture in the liquid phase. The mixture is allowed to stand for approximately 24 hours. No phase separation is observed.

EXAMPLE 1

A mixture of hydrofluoric acid, sulfolane, and ASO (having the same composition as the mixture of the Comparative Example, above) is charged to a stripping tower having three theoretical stages. Isobutane is introduced into the tower at a level below the height of the liquid (HF/sulfolane/ASO) charge point, and the isobutane and mixture charge rates are controlled to maximize stripping of HF while operating below the flooding point of the tower. A stripped liquid is withdrawn from the bottom of the tower and a HF-enriched isobutane stream is withdrawn from the top of the tower. The stripped liquid contains less than about 30 percent by weight of hydrofluoric acid.

The stripped liquid is then charged to a decantation vessel and allowed to stand for approximately 24 hours. The mixture separates into two distinct phases, an upper, less dense ASO-enriched phase, and a lower, more dense, sulfolane-enriched phase.

EXAMPLES 2-4

Additional samples of the mixture of hydrofluoric acid, sulfolane, and ASO (having the same composition as the mixture of the Comparative Example) are stripped with isobutane to hydrofluoric acid contents of 25 weight percent, 10 weight percent, and 5 weight percent, respectively. The stripped mixtures containing lower concentrations of hydrofluoric acid separate into more highly purified sulfolane-enriched and ASO-enriched phases.

EXAMPLE 5

The HF/sulfolane sample of Example 5 has the following composition:
HF 62 wt. %
Sulfolane 27 wt. %
Isobutane 4 wt. %
Water 1-2 wt. %
ASO 3 wt. %
Balance to 100% other hydrocarbons. This mixture is a single liquid phase at 90° F. and 120 psig.

The sample is brought to atmospheric pressure and room temperature and most of the light hydrocarbons and part of the HF are vented off. Under these conditions, the sample is a single liquid phase containing about 50 wt. % HF.

Nitrogen is then bubbled through the mixture at room temperature and atmospheric pressure to strip HF off the mixture. As the mixture is depleted in HF, the mixture separates into two phases. In Example 5, the two phases appear within several minutes of the HF concentration reaching about 2 wt. %.

Both phases are analyzed, and the dense phase (specific gravity about 1.26) contains 83.2 wt. % sulfolane, 2.2 wt. % ASO, and the balance water, salts, and a sludge. The lighter phase, having a density of less than about 1, contains B2.8 wt. % ASO, 13.3 wt. % sulfolane, and the balance of salts.

Figures 2A, 2B, 2C:
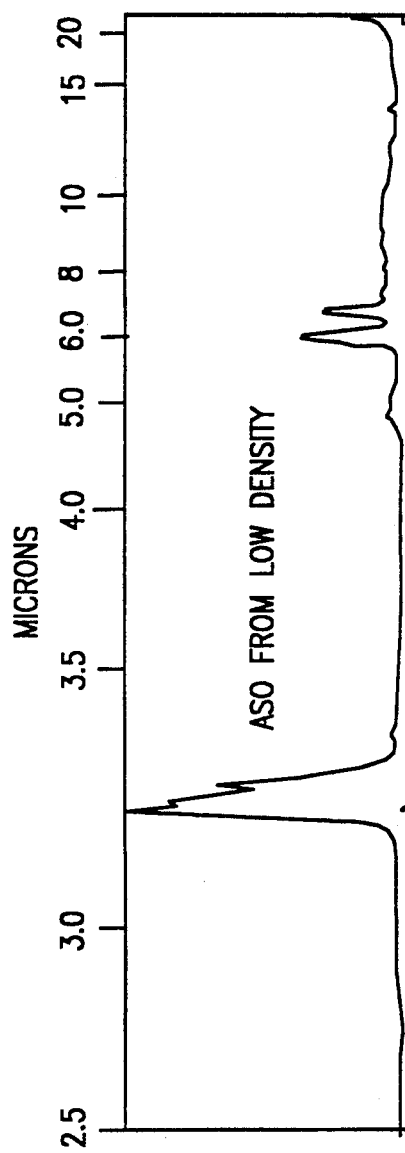
FIG. 2A shows the infrared (IR) spectrum of the conjunct polymer from the lower-density phase withdrawn from gravitational separation following stripping without nonpolar solvent extraction.
FIG. 2B shows the IR spectrum of the higher density phase withdrawn from the gravitational separation step of the invention.
FIG. 2C shows the IR spectrum of sulfolane extracted from the higher density phase withdrawn from the gravitational step of the invention.

FIG. 2 shows the IR spectra of ASO from the lighter phase (the upper spectrum), ASO from the heavier phase (the middle spectrum) and sulfolane (the lower spectrum).

Figure 3:
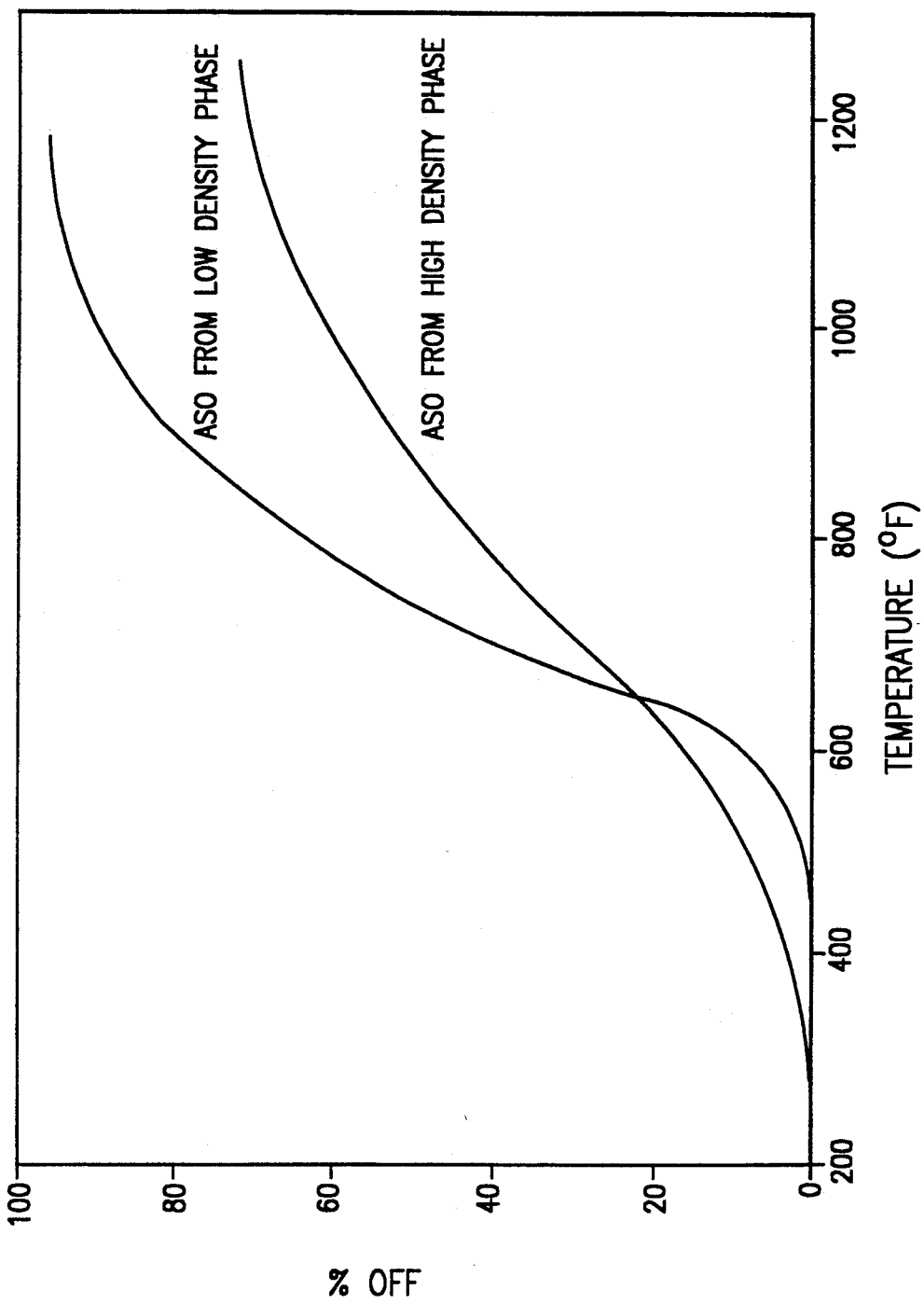
FIG. 3 shows a simulated distillation comparing the boiling ranges of components in the conjunct polymeric byproducts (also referred to herein as acid soluble oil or ASO) from the lower density phase of the gravitational separation step with the ASO from the higher density phase of the gravitational separation step of the invention.

FIG. 3 shows simulated distillations of ASO fractions from the low density phase and the high density phase from the gravitational separation step. The initial boiling point and the endpoint for the low density phase are both lower than the corresponding points for the high density phase. Thus the gravitational separation splits the ASO into two fractions having different, albeit overlapping, boiling ranges. Thus while the feedstream to the gravitational separation step cannot be distilled to isolate sulfolane, the boiling range of the ASO fraction contained in the more dense phase withdrawn from the gravitational separation step overlaps the boiling point of sulfolane only slightly (or preferably, not at all).

EXAMPLE 6

A mixture of HF, sulfolane, and ASO is stripped of HF and then admixed with toluene to provide the following composition:

| Sulfolane | 43 wt. % |
| ASO | 27 wt. % |
| Toluene | 30 wt. % |

The mixture is then charged to a gravitational separator where it forms two substantially immiscible phases having the following compositions:

| Heavy phase: | |
| Sulfolane | 76 wt. % |
| ASO | 12 wt. % |
| Toluene | 12 wt. % |
| Light phase: | |
| Sulfolane | 4 wt. % |

| -continued | |
|---|---|
| ASO | 40 wt. % |
| Toluene | 55 wt. %. |

The results of Example 6 are surprising because the majority of the toluene extraction solvent is found in the light phase with the ASO. This result is unusual because sulfolane is commonly used in industry as an extraction solvent for aromatics, and toluene is one of the aromatics which sulfolane is known to extract. In contrast, Example 6 shows toluene and sulfolane to behave differently in the presence of ASO than would be predicted from their well-known behavior in the absence of ASO.

EXAMPLE 7

In Example 7, sulfolane, ASO, and alkylate were mixed and then allowed to separate into two phases which were divided using a separatory funnel and weighed. The feed and products were as follows:

| Feed | |
|---|---|
| Compound | Weight, gms |
| Sulfolane | 15.23 |
| ASO | 1.55 |
| Alkylate | 1.49 |

| | Product | |
|---|---|---|
| Compound | Sulfolane Rich Product: Weight, gms | ASO Rich Product: Weight, gms |
| Sulfolane | 14.99 | 0.11 |
| ASO + Alkylate | 0.35 | 2.31 |

Losses during separation accounted for about 0.5 grams of material. This extraction experiment shows excellent separation with over 98% of the sulfolane was recovered and less than 12% of the ASO and alkylate remaining in the sulfolane phase.

Changes and modifications in the specifically described embodiments can be carried out without departing from the scope of the invention which is intended to be limited only by the scope of the appended claims.

What is claimed is:

1. A method for separating conjunct polymers which are formed as byproducts of acid catalyzed isoparaffin-olefin alkylation and sulfolane from a mixture containing conjunct polymers, sulfolane, and hydrofluoric acid comprising the sequential steps of:
   (a) removing hydrofluoric acid from a mixture containing sulfolane, conjunct polymers and hydrofluoric acid to provide a first intermediate stream containing less than about 30 percent hydrofluoric acid by weight;
   (b) mixing said intermediate stream with a nonpolar extraction solvent to provide a second intermediate stream; and
   (c) gravitationally separating said intermediate stream into a less dense extract stream enriched conjunct polymers and a more dense liquid stream enriched in sulfolane.

2. The method of claim 1 wherein said nonpolar extraction solvent is characterized by a dipole moment of less than about 0.6 debyes.

3. The method of claim 1 wherein said nonpolar extraction solvent comprises at least one aliphatic or aromatic hydrocarbon.

4. The method of claim 2 wherein said nonpolar extraction solvent comprises at least one paraffin having from about 4 to about 12 carbon atoms.

5. The method of claim 4 wherein said nonpolar extraction solvent comprises trimethylpentane.

6. The method of claim 4 wherein said nonpolar extraction solvent comprises the alkylate product formed by reacting an isoparaffin with an olefin.

7. The method of claim 4 wherein said nonpolar extraction solvent comprises an aromatic hydrocarbon having one substituted benzene ring.

8. The method of claim 7 wherein said nonpolar extraction solvent comprises toluene.

9. The method of claim 1 wherein said hydrofluoric acid is separated from said mixture by countercurrently contacting said mixture with a stripping fluid.

10. The method of claim 9 wherein said stripping fluid is selected from the group consisting of normal paraffins and isoparaffins.

11. The method of claim 10 wherein said stripping fluid is selected from the group consisting of normal butane and isobutane.

12. The method of claim 9 wherein said stripping step comprises sequentially stripping said mixture with isoparaffin and then stripping said mixture with nitrogen.

13. The method of claim 1 wherein said hydrofluoric acid separation step provides an intermediate stream containing less than about 25 percent hydrofluoric acid by weight.

14. The method of claim 13 wherein said hydrofluoric acid separation step provides an intermediate stream containing less than about 10 percent hydrofluoric acid by weight.

15. The method of claim 14 wherein said hydrofluoric acid separation step provides an intermediate stream containing less than about 5 percent hydrofluoric acid by weight.

* * * * *

UNITED STATES PATENT AND TRADEMARK OFFICE
CERTIFICATE OF CORRECTION

PATENT NO. : 5,264,650

DATED : November 23, 1993

INVENTOR(S) : M. A. Better et al.

It is certified that error appears in the above-identified patent and that said Letters Patent is hereby corrected as shown below:

Col. 8, line 7, after "enriched" insert --in--

Signed and Sealed this

Thirty-first Day of May, 1994

Attest:

BRUCE LEHMAN

*Attesting Officer*     *Commissioner of Patents and Trademarks*